(12) United States Patent
Wagner

(10) Patent No.: US 7,437,909 B2
(45) Date of Patent: Oct. 21, 2008

(54) OSCILLATORY MEASUREMENT DEVICE WITH VISUAL RECORDER

(75) Inventor: Jeff Wagner, Washington Township, Morris City, NJ (US)

(73) Assignee: Rudolph Research Analytical, Hackettstown, NJ (US)

( * ) Notice: Subject to any disclaimer, the term of this patent is extended or adjusted under 35 U.S.C. 154(b) by 6 days.

(21) Appl. No.: 11/471,320

(22) Filed: Jun. 20, 2006

(65) Prior Publication Data

US 2007/0289376 A1   Dec. 20, 2007

(51) Int. Cl.
*G01N 9/00* (2006.01)

(52) U.S. Cl. ........................................ 73/32 A

(58) Field of Classification Search .................. 73/32 A, 73/19.01, 19.03, 19.1
See application file for complete search history.

(56) References Cited

U.S. PATENT DOCUMENTS

| | | | |
|---|---|---|---|
| 4,074,562 A * | 2/1978 | North, Jr. ..................... | 73/32 A |
| 6,629,449 B1 * | 10/2003 | Kline-Schoder et al. ... | 73/19.03 |
| 6,843,099 B2 * | 1/2005 | Derek et al. ................ | 73/19.01 |

* cited by examiner

*Primary Examiner*—John E Chapman
(74) *Attorney, Agent, or Firm*—Kaplan Gilman Gibson & Dernier LLP

(57) ABSTRACT

An oscillatory measurement system is disclosed that includes a visual recorder for detecting irregularities such as bubbles in a fluid to be measured. Techniques are provided for scanning the recorder across the oscillatory tube.

14 Claims, 1 Drawing Sheet

OSCILLATORY MEASUREMENT DEVICE WITH VISUAL RECORDER

TECHNICAL FIELD

This invention relates to density measurement, and more specifically, to an improved method and apparatus for using an oscillator to measure density or other parameters of a fluid.

BACKGROUND OF THE INVENTION

A common form of density measuring instrument is the vibrating tube type wherein a hollow oscillator is filled with a sample under test. The density is determined from a parameter of the oscillator, typically the frequency or period of oscillation.

FIG. 1 illustrates a typical such prior art arrangement. A cantilevered hollow oscillator 1 is formed of transparent material and mounted to a support 2. This support forms a node in the oscillator which defines the volume of the sample under test. Means to sustain and measure the oscillation are well known and are omitted for clarity. Rectangular area 3 represents the area viewable by the operator through a window or viewport.

Sample entrance and exit ports 4 allow introduction of the sample under test. The sample flows around the U-tube shape as shown.

The presence of small bubbles or particulates anywhere in the oscillating sample can cause errors in the density measurement. Consequently, these instruments are often constructed with clear glass oscillators and viewing windows to allow the user to visually scan the sample for bubbles or particulates during and after injection of the sample under test.

The small physical size of the bubbles makes this difficult. Furthermore the density measuring apparatus is often placed in an environment that makes viewing inconvenient, for example under a fume hood.

DETAILED DESCRIPTION OF THE PREFERRED EMBODIMENT

A video camera and display may be used to create an expanded remotable view of the oscillator. Two practical problems must be overcome to implement such a system. First, the ratio of the length of the sample filled oscillator, typically 75 mm, to the size of a small bubble of perhaps $\frac{1}{10}$ of a millimeter is very high. A magnification that would allow convenient viewing of the bubble, for example 20 times, would result in an overall image size of 1.5 meters. This size and cost of such a display is not suitable for integration into a bench-top density meter. Second, to resolve such small bubbles requires that each bubble be imaged over several pixels of the camera. Using the example figures above the resolution of the camera and display would need to be over 2000 pixels. Such cameras exist, but their cost is prohibitive. The current invention discloses a way to overcome these difficulties and provide a means of ensuring that the full length of the oscillating sample is free from small bubbles and particulates.

Figure 1:
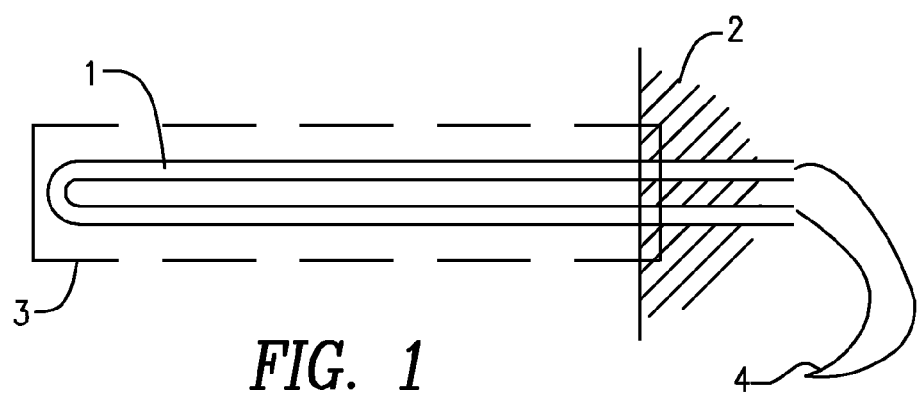
FIG. 1 is a depiction of a prior art oscillatory measurement device.
Figure 2:
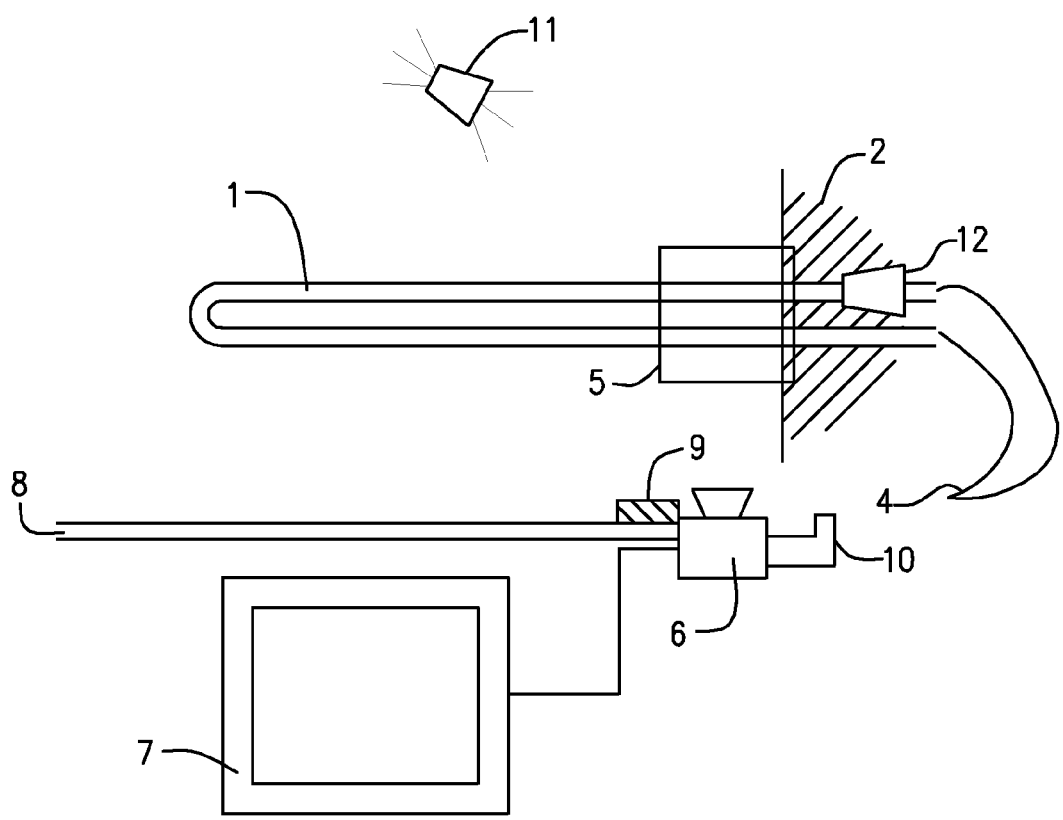
FIG. 2 depicts an exemplary embodiment of the present invention.

FIG. 2 illustrates an exemplary embodiment of the present invention. Here rectangular area 5 represents a view of a greatly reduced portion of the cantilevered hollow oscillator 1 adjacent to the node formed by support 2 including a view of the entrance and exit flows. The view of rectangular area 5 is transferred by camera and optics 6 to display 7.

Reducing the size of the viewed area reduces the required display size and camera resolution for a given magnification. For example a 16 mm wide viewing area imaged onto a 640 pixel wide camera would resolve a $\frac{1}{10}$ mm bubble over four pixels. At a magnification of 20 times the display would be 320 mm wide. Cameras and displays of these dimensions are economical and convenient to integrate into bench-top instrumentation.

Positioning the reduced viewed area adjacent to the node which defines the sample volume and including views of the entrance and exit flows allows the operator to scan the sample for bubbles and particulates as it is loaded. If a bubble or particulate is observed entering the oscillator, loading must continue until the bubble or particulate is observed exiting the oscillator. By this method the operator is assured that no bubbles or particulates have been introduced anywhere in the oscillator.

The detection of bubbles or particulates may be automated, as by utilizing software that detects irregularities via image processing, and can assure that a similar irregularity exits the oscillatory tube 1 prior to measurement.

In some cases bubbles may form in the sample after loading. For instance a dissolved gas may come out of solution as a sample cools. For this case the reduced field of view may be scanned across the oscillator for example by placing the camera and optics on a linear slide 8 operated either by hand or by an actuator 9. Alternatively, the field of view of the camera 6 may be physically large enough to capture the entire oscillatory tube, but the actual field of view may be controlled and limited electronically to the field show as 5 in FIG. 2.

It is also noted that the camera may be controlled electronically so that at a particular point of the measurement process, such as when fluid begins being introduced into oscillatory tube 1, the camera begins to capture the moving image. Or, when the oscillatory tube is filled, the camera 6 automatically begins to scan the entire oscillatory tube 1. Or, both may occur as well.

As shown in the figure and necessary to the operation of the invention is a means of illuminating the area viewed by the camera. An illumination system that allows the operator to vary the balance between bright field 11 and dark field 10 illumination is preferred. Additionally, light from a source 12 may be conducted into the viewed area by using the sample and oscillator ports as a light pipe. Light conducted along the sample is deflected by bubbles toward the camera.

The above describes the preferred embodiment. The oscillator shown may be replaced with any other type of oscillator, such as that described in the U.S. patent application No. 11/471,355 entitled Method and Apparatus for Oscillating a Test Sample, filed concurrently herewith and owned by the same assignee of the present application.

The invention claimed is:

1. An apparatus for measuring the density of fluids comprising:
    a hollow oscillator filled with a sample under test mounted on a support,
    a camera arranged to give a magnified view of a portion of said oscillator as said oscillator is filled with fluid, and
    a display for exhibiting said magnified view from said camera, wherein said magnified view includes the entrance and exit ports and an area adjacent said entry and exit ports and wherein said magnified view excludes a majority of said hollow oscillator.

2. The apparatus in claim 1 further comprising a means of scanning the viewed area along the length of the oscillator.

3. The apparatus of claim 2 wherein said means of scanning the viewed area is a linear slide actuated by an electric motor.

4. The apparatus of claim 2 wherein said means of scanning the viewed area is a linear slide actuated manually.

5. The apparatus of claim 1 further comprising a window for direct view by an operator of the sample filled oscillator.

6. Apparatus of claim 1 wherein said hollow oscillator is at least partly in the shape of a U.

7. An apparatus for measuring the density of fluids comprising:
   a hollow oscillator filled with a sample under test mounted on a support,
   a camera arranged to give a magnified view of a portion of said oscillator as said oscillator is filled with fluid, said view including a view of the entrance and exit ports and
   a display for exhibiting said magnified view from said camera, said view excluding a majority of said oscillator.

8. The apparatus of claim 6 wherein said means of illumination is a dark field illumination system.

9. The apparatus of claim 6 wherein said means of illumination is a bright field illumination system.

10. An apparatus for measuring the density of fluids comprising:
    a hollow oscillator filled with a sample under test mounted on a support,
    a camera arranged to give a magnified view of a portion of said oscillator as said oscillator is filled with fluid, and for an amount of time sufficient for fluid entering said hollow oscillator to exit, said view including a view of the entrance and exit ports
    a display for exhibiting said magnified view from said camera, the apparatus further comprising a means of illuminating the viewed are and wherein said means of illumination includes light conducted along the sample filled oscillator in the manner of a light pipe.

11. An apparatus for measuring the density of fluids comprising:
    a hollow oscillator filled with a sample under test mounted on a support,
    a camera arranged to give a magnified view of a portion of said oscillator as said oscillator is filled with fluid, and for an amount of time sufficient for fluid entering said hollow oscillator to exit, said view including a view of the entrance and exit ports and
    a display for exhibiting said magnified view from said camera; and software configured to detect a bubble at an entrance port and to also detect said bubble exiting said oscillator prior to a measurement being taken.

12. The method of claim 11 wherein said software includes software for displaying said bubble.

13. A hollow oscillator comprising a tube for holding fluid and a visual recorder arranged to scan over said tube from one end to another, means for detecting bubbles and means for recording two instances of every detected bubble, prior to use of said oscillator for measurement of fluid density further comprising software configured to detect a bubble at an entrance port and to also detect said bubble exiting said oscillator prior to a measurement being taken.

14. The method of claim 13 wherein said software includes software for displaying said bubble.

* * * * *